(12) United States Patent
Barba et al.

(10) Patent No.: US 8,367,083 B2
(45) Date of Patent: Feb. 5, 2013

(54) COSMETIC MAKEUP AND/OR CARE METHOD USING A SILOXANE RESIN AND A PHENYL SILICONE OIL

(75) Inventors: Claudia Barba, Paris (FR); Roberto Cavazzuti, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/746,285

(22) PCT Filed: Dec. 5, 2008

(86) PCT No.: PCT/FR2008/052220
§ 371 (c)(1),
(2), (4) Date: Nov. 3, 2010

(87) PCT Pub. No.: WO2009/080953
PCT Pub. Date: Jul. 2, 2009

(65) Prior Publication Data
US 2011/0038820 A1    Feb. 17, 2011

Related U.S. Application Data

(60) Provisional application No. 60/992,357, filed on Dec. 5, 2007.

(51) Int. Cl.
*A61K 8/02* (2006.01)
(52) U.S. Cl. ............... 424/401; 528/10; 528/14; 528/39
(58) Field of Classification Search .................. None
See application file for complete search history.

(56) References Cited

U.S. PATENT DOCUMENTS

| | | | |
|---|---|---|---|
| 2004/0151680 | A1 | 8/2004 | Patil et al. |
| 2006/0045893 | A1* | 3/2006 | Yu et al. ............... 424/401 |
| 2006/0228314 | A1 | 10/2006 | Patil et al. |
| 2006/0292096 | A1 | 12/2006 | Yu |
| 2007/0258933 | A1 | 11/2007 | Bui et al. |
| 2010/0247460 | A1* | 9/2010 | Lin et al. ............... 424/59 |

FOREIGN PATENT DOCUMENTS

| | | |
|---|---|---|
| EP | 1 498 103 | 1/2005 |
| WO | 2005 075542 | 8/2005 |
| WO | 2005 075567 | 8/2005 |
| WO | WO 2005/100444 | * 10/2005 |
| WO | 2009 071662 | 6/2009 |

OTHER PUBLICATIONS

Caprasse, V. et al., "A New Silicone Resin for Personal Care Applications", Research Disclosure, Research Disclosure Database No. 486008, vol. 486, No. 8, Total pp. 7, (Oct. 1, 2004) XP 007134333 ISSN 0374-4353.

Steinbach, K. et al., "Verwendung Von IR-Reflektierenden Pigmenten in Kosmetischen Applikationen", Research Disclosure, Research Disclosure Database No. 523005, vol. 523, No. 5, Total pp. 9 (Nov. 1, 2007) XP 007137714 ISSN 0374-4353.

Kowandy, V. et al. "Bodied MQ-T Propyl Silicone Resins in Color Cosmetic Applications", IP. Com. Journal, PriorArtDatabase, IP. com No. IPCOM000177062D, pp. 1-15, (Dec. 4, 2008) XP 013127272 ISSN: 1533-0001.

Fang, Z. K. et al., " New Formulation Capabilities With Three New Silicone Resin Flake Products", IP. Com. Journal, PriorArtDatabase, IP. com No. IPCOM000177038D, Total pp. 17, (Dec. 4, 2008) XP 013128295 ISSN: 1533-0001.

U.S. Appl. No. 12/746,324, filed Jun. 4, 2010, Barba et al.
U.S. Appl. No. 12/746,413, filed Jun. 4, 2010, Barba et al.
U.S. Appl. No. 12/746,282, filed Jun. 4, 2010, Barba.
U.S. Appl. No. 12/746,613, filed Jun. 7, 2010, Barba et al.

* cited by examiner

*Primary Examiner* — Bethany Barham
(74) *Attorney, Agent, or Firm* — Oblon, Spivak, McClelland, Maier & Neustadt, L.L.P.

(57) ABSTRACT

The present invention relates to a process for making up and/or caring for keratin materials, in which a composition is applied to the keratin materials, and especially to the lips, this composition containing, in a physiologically acceptable medium:

a) a siloxane resin comprising the following units:
  (i) $(R^1{}_3SiO_{1/2})_a$
  (ii) $(R^2{}_2SiO_{2/2})_b$
  (iii) $(R^3SiO_{3/2})_c$ and
  (iv) $(SiO_{4/2})_d$ with
  $R^1$, $R^2$ and $R^3$ independently representing an alkyl group containing from 1 to 8 carbon atoms, an aryl group, a carbinol group or an amino group,
  a being between 0.05 and 0.5,
  b being between 0 and 0.3,
  c being greater than 0,
  d being between 0.05 and 0.6,
  $a+b+c+d=1$,
  on condition that more than 40 mol % of the groups $R^3$ of the siloxane resin are propyl groups, and
b) at least one phenyl silicone oil.

15 Claims, No Drawings

COSMETIC MAKEUP AND/OR CARE METHOD USING A SILOXANE RESIN AND A PHENYL SILICONE OIL

The invention relates to a cosmetic composition for keratin materials, especially the skin, the hair and the nails. The invention relates in particular to makeup compositions for keratin materials.

One of the objects of the patent application is to produce makeup compositions for keratin materials (skin, mucous membranes, fibre, eyelashes and integuments) that allow the application of a total transfer-resistant film which is glossy and comfortable and has good staying power.

In the field of lipsticks and foundations, formulators are in search of compositions that have good staying power properties. These compositions must also be transfer resistant, while at the same time offering good comfort properties to satisfy consumer demands.

Moreover, more specifically in the field of lipsticks, it is sought to obtain compositions that have a good level of gloss or a good gloss effect. This gloss, which brings out the beauty of the lips, is generally obtained by formulating glossy oils and/or particles with glints. When formulation is performed with glossy oils, the makeup formulations then have the characteristic of being tacky. This tacky nature causes these formulations to leave marks on supports, for instance glasses or coffee cups.

Formulators are thus in search of starting materials and/or systems that can produce compositions whose deposit is characterized by comfort, gloss and long staying power.

It is known to those skilled in the art to use polymers in order to obtain these properties of staying power in the course of the day.

These polymers are of very different chemical nature and are conveyed either in a fatty phase or in an aqueous phase.

Mention may be made, for example, of silicone resins especially of MQ type, polyacrylates, latices, etc.

Although these polymers do indeed provide staying power properties, in particular transfer-resistance properties, they are usually accompanied by drawbacks either during the application of the product (difficult spreading, tack, etc.) or in the course of the day (tautness, mask effect, etc.).

It is thus necessary to seek a technical solution for obtaining these staying power properties while at the same time maintaining comfortable use.

These objects, and others, are achieved by means of a composition containing, in a physiologically acceptable medium, a) a siloxane resin comprising the following units:
 (i) $(R^1{}_3SiO_{1/2})_a$
 (ii) $(R^2{}_2SiO_{2/2})_b$
 (iii) $(R^3SiO_{3/2})_c$ and
 (iv) $(SiO_{4/2})_d$
with
$R^1$, $R^2$ and $R^3$ independently representing an alkyl group containing from 1 to 8 carbon atoms, an aryl group, a carbinol group or an amino group,
 a being between 0.05 and 0.5,
 b being between 0 and 0.3,
 c being greater than 0,
 d being between 0.05 and 0.6,
 a+b+c+d=1,
 on condition that more than 40 mol % of the groups $R^3$ of the siloxane resin are propyl groups, and
b) at least one phenyl silicone oil.

Preferably, the siloxane resin comprises the following units:
 (i) $(R^1{}_3SiO_{1/2})_a$
 (iii) $(R^3SiO_{3/2})_c$ and
 (iv) $(SiO_{4/2})_d$
with
$R^1$ and $R^3$ independently representing an alkyl group containing from 1 to 8 carbon atoms, $R^1$ preferably being a methyl group and $R^3$ preferably being a propyl group,
 a being between 0.05 and 0.5 and preferably between 0.15 and 0.4,
 c being greater than zero, preferably between 0.15 and 0.4,
 d being between 0.05 and 0.6, preferably between 0.2 and 0.6 or alternatively between 0.2 and 0.55,
 a+b+c+d=1,
 on condition that more than 40 mol % of the groups $R^3$ of the siloxane resin are propyl groups.

The siloxane resins that may be used according to the invention may be obtained via a process comprising the reaction of:
 A) an MQ resin comprising at least 80 mol % of units $(R^1{}_3SiO_{1/2})_a$ and $(SiO_{4/2})_d$
  $R^1$ representing an alkyl group containing from 1 to 8 carbon atoms, an aryl group, a carbinol group or an amino group,
  a and d being greater than zero,
  the ratio a/d being between 0.5 and 1.5; and
 B) a propyl resin T comprising at least 80 mol % of units $(R^3SiO_{3/2})_c$,
  $R^3$ representing an alkyl group containing from 1 to 8 carbon atoms, an aryl group, a carbinol group or an amino group,
  c being greater than zero,
  on condition that at least 40 mol % of the groups $R^3$ are propyl groups,
in which the mass ratio A/B is between 95/5 and 15/85 and preferably the mass ratio A/B is 30/70.

Advantageously, the mass ratio A/B is between 95/5 and 15/85. Preferably, the ratio A/B is less than or equal to 70/30. These preferred ratios have proven to afford comfortable deposits due to the absence of percolation of the rigid particles of MQ resin in the deposit.

The compositions according to the invention may be in various forms, especially in the form of a powder, an anhydrous dispersion, a water/oil, water/wax, oil/water, multiple or wax/water emulsion, or a gel.

The resins that may be used according to the invention are especially those described in patent application WO 2005/075 542, the content of which is incorporated herein by reference.

The MQ-T propyl resin a) according to the invention comprises the following units:
 (i) $(R^1{}_3SiO_{1/2})_a$
 (ii) $(R^2{}_2SiO_{2/2})_b$
 (iii)) $(R^3SiO_{3/2})_c$ and
 (iv) $(SiO_{4/2})_d$
which are known in the prior art and which correspond, respectively, to M, D, T and Q units.

The amount of each unit present in the MQ-T propyl resin a) may be expressed as a mole fraction (i.e. a, b, c or d) of the total number of moles of all the units M, D, T and Q present in the MQ-T propyl resin a).

The value of a (mole fraction of M units) is between 0.05 and 0.5, or alternatively between 0.15 and 0.4.

The value of b (mole fraction of D units) is between 0 and 0.3, alternatively between 0 and 0.1, or alternatively between 0 and 0.05. Thus, the MQ-T propyl resin a) according to the invention may be free of D units, or alternatively may comprise up to 0.3 mole fraction of D units.

Preferably, the MQ-T propyl resin a) according to the invention is free of D units.

The value of c (mole fraction of T units) is greater than 0, alternatively between 0.05 and 0.65, or alternatively between 0.4 and 0.65.

The value of d (mole fraction of Q units) is between 0.05 and 0.6, alternatively between 0.2 and 0.6, or alternatively between 0.2 and 0.55.

The MQ-T propyl resin a) according to the invention is characterized in that at least 40 mol %, preferably at least 50 mol % and preferably at least 90 mol % of alkyl groups $R_3$ of the T units are propyl groups.

The radicals $R^1$, $R^2$ and $R^3$ of the units of the MQ-T propyl resin independently represent an alkyl group containing from 1 to 8 carbon atoms, an aryl group, a carbinol group or an amino group.

The alkyl groups may be chosen especially from methyl, ethyl, propyl, butyl, pentyl, hexyl and octyl groups. Preferably, the alkyl group is a methyl group or a propyl group.

The aryl groups may be chosen from phenyl, naphthyl, benzyl, tolyl, xylyl, xenyl, methylphenyl, 2-phenylethyl, 2-phenyl-2-methylethyl, chlorophenyl, bromophenyl and fluorophenyl groups, the aryl group preferentially being a phenyl group.

In the present invention, the term "carbinol group" means any group containing at least one hydroxyl radical bonded to a carbon (COH). The carbinol groups may thus contain more than one COH radical, for instance

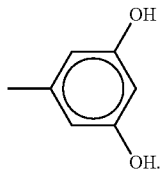

If the carbinol group is free of aryl groups, it comprises at least 3 carbon atoms. If the carbinol group comprises at least one aryl group, it comprises at least 6 carbon atoms.

As examples of carbinol groups free of aryl groups and comprising at least 3 carbon atoms, mention may be made of the groups of formula $R^4OH$ in which $R^4$ represents a divalent hydrocarbon-based radical comprising at least 3 carbon atoms or a divalent hydrocarbonoxy radical comprising at least 3 carbon atoms. As examples of groups $R^4$, mention may be made of alkylene radicals such as $-(CH_2)_x-$, the value of x being between 3 and 10, $-CH_2CH(CH_3)-$, $-CH_2CH(CH_3)CH_2-$, $-CH_2CH_2CH(CH_2CH_3)CH_2CH_2CH_2-$ and $-OCH(CH_3)(CH_2)_x-$, the value of x being between 1 and 10.

As examples of carbinol groups comprising aryl groups bearing at least 6 carbon atoms, mention may be made of the groups of formula $R^5OH$ in which $R^5$ represents an arylene radical such as $-(CH_2)_xC_6H_4-$, x having a value between 0 and 10, $-CH_2CH(CH_3)(CH_2)_xC_6H_4-$, x having a value of between 0 and 10, $-(CH_2)_xC_6H_4(CH_2)_x-$, x having a value between 1 and 10. The carbinol groups comprising aryl groups generally comprise from 6 to 14 atoms.

According to the invention, the term "amino group" especially means groups of formula $-R^6NH_2$ or $-R^6NHR^7NH_2$, $R^6$ representing a divalent hydrocarbon-based radical containing at least 2 carbon atoms and $R^7$ representing a divalent hydrocarbon-based radical containing at least 2 carbon atoms. The group $R^6$ generally represents an alkylene radical containing from 2 to 20 carbon atoms. Examples of groups $R^6$ that may be mentioned include ethylene, propylene, $-CH_2CHCH_3-$, butylene, $-CH_2CH(CH_3)CH_2-$, pentamethylene, hexamethylene, 3-ethylhexamethylene, octamethylene and decamethylene groups.

The group $R^7$ generally represents an alkylene radical containing from 2 to 20 carbon atoms. Examples of groups $R^7$ that may be mentioned include ethylene, propylene, $-CH_2CHCH_3-$, butylene, $-CH_2CH(CH_3)CH_2-$, pentamethylene, hexamethylene, 3-ethylhexamethylene, octamethylene and decamethylene groups.

The amino groups are generally $-CH_2CH_2CH_2NH_2$ and $-CH_2(CH_3)CHCH_2(H)NCH_3$, $-CH_2CH_2NHCH_2CH_2NH_2$, $-CH_2CH_2NH_2$, $-CH_2CH_2NHCH_3$, $-CH_2CH_2CH_2CH_2NH_2$, $-(CH_2CH_2NH)_3H$ and $-CH_2CH_2NHCH_2CH_2NHC_4H_9$.

Preferably, $R^1$ represents a methyl group, $R^2$ represents a methyl group or a phenyl group, and $R^3$ represents a propyl group.

Preferably, the MQ-T propyl resin a) according to the invention is free of units D, and $R^1$ represents a methyl group, and $R^3$ represents a propyl group.

The siloxane units D, T or Q of the MQ-T propyl resin a) according to the invention may comprise hydroxyl groups (—OH) and/or alkoxy groups. Such siloxane units comprising hydroxyl and/or alkoxy groups are commonly present in siloxane resins having the general formula $R_nSiO_{(4-n)/2}$.

These hydroxyl groups typically result from the reaction of a hydrolysable group on the siloxane unit with water; the alkoxy groups result from an incomplete hydrolysis when alkoxysilane precursors are used or result from the exchange of alcohol with hydrolysable groups.

Preferably, the total amount by weight of —OH groups present in the MQ-T propyl resin is about 3%, preferably 2% and preferably 1.5%. Preferably, the total amount by weight of alkoxy groups present in the MQ-T propyl resin is less than or equal to 20% by weight and preferably less than or equal to 10% by weight.

There are no restrictions relating to the molecular mass of the MQ-T propyl siloxane resins, but the number-average molecular mass ($M_n$) is generally between 3000 and 10 000 or alternatively between 5000 and 8000.

The MQ-T propyl resins that are suitable for use as component a) may be prepared according to the processes known in the prior art for preparing siloxane resins of general formula $R_nSiO_{(4-n)/2}$ in which R is an alkyl group and n is less than 1.8.

Alternatively, the MQ-T propyl resins may be prepared according to the methods described below.

The MQ-T propyl resins a) according to the invention are illustrated by the MQ-T propyl resins comprising the following units:
$((CH_3)_3SiO_{1/2})_a$
$(R^3SiO_{3/2})_c$ in which $R^3$=$CH_3CH_2CH_2-$, and
$(SiO_{4/2})_d$;
or the following units:
$((CH_3)_3SiO_{1/2})_a$
$((CH_3)_2SiO_{2/2})_b$
$(R^3SiO_{3/2})_c$ in which $R^3$=$CH_3CH_2CH_2-$, and
$(SiO_{4/2})_d$;
or the following units:
$((CH_3)_3SiO_{1/2})_a$
$((CH_3)_2SiO_{2/2})_b$, $((CH_3)(C_6H_5)SiO_{2/2})_b'$
$(R^3SiO_{3/2})_c$ in which $R^3$=$CH_3CH_2CH_2-$, and $(SiO_{4/2})_d$;

or the following units:

$((CH_3)_3SiO_{1/2})_a$
$((CH_3)_2SiO_{2/2})_b$
$(R^3SiO_{3/2})_c$ in which $R^3$=$CH_3CH_2CH_2$—, and
$(C_6H_5SiO_{3/2})_c$
$(SiO_{4/2})_d$;

or the following units:

$((CH_3)_3SiO_{1/2})_a$
$((CH_3)_2SiO_{2/2})_b$, $((CH_3)(C_6H_5)SiO_{2/2})_{b'}$
$(R^3SiO_{3/2})_c$ in which $R^3$=$CH_3CH_2CH_2$—, and
$(C_6H_5SiO_{3/2})_c$
$(SiO_{4/2})_d$;

in which a has a total value in the resin of between 0.05 and 0.5, the sum b+b' has a total value in the resin of between 0 and 0.3, c has a total value in the resin of between 0.05 and 0.65 and d has a total value in the resin of between 0.05 and 0.6.

The siloxane resins that may be used according to the invention may be obtained via a process comprising the reaction between:

A) an MQ resin comprising at least 80 mol % of units $(R^1{}_3SiO_{1/2})_a$ and $(SiO_{4/2})_d$ $R^1$ representing an alkyl group containing from 1 to 8 carbon atoms, an aryl group, a carbinol group or an amino group, a and d being greater than zero, the ratio a/d being between 0.5 and 1.5;

and

B) a T propyl resin comprising at least 80 mol % of units $(R^3SiO_{3/2})_c$, $R^3$ representing an alkyl group containing from 1 to 8 carbon atoms, an aryl group, a carbinol group or an amino group, c being greater than zero, on condition that at least 40 mol % of the groups $R^3$ are propyl groups, in which the mass ratio A/B is between 95/5 and 15/85.

Component A) is an MQ resin comprising at least 80 mol of units $(R^1{}_3SiO_{1/2})_a$ and $(SiO_{4/2})_d$ in which $R^1$ is as defined above, i.e. it represents an alkyl group containing from 1 to 8 carbon atoms, an aryl group, a carbinol group or an amino group, a and d being greater than zero, and the ratio a/d being between 0.5 and 1.5.

The MQ resins that may be used as component A), and the method for preparing them, are known in the prior art. For example, U.S. Pat. No. 2,814,601, belonging to Currie et al., dated 26 Nov. 1957, describes a process for manufacturing MQ resins by transformation of a water-soluble silicate into a silicic acid monomer or a silicic acid oligomer using an acid. Once the appropriate polymerization has been performed, trimethylchlorosilane end groups are introduced to obtain the MQ resin. Another process for preparing MQ resins is described in U.S. Pat. No. 2,857,356 belonging to Goodwin, dated 21 Oct. 1958. Goodwin describes a process for manufacturing an MQ resin by cohydrolysis of a mixture of an alkyl silicate and an organopolysiloxane trialkylsilane that is hydrolysable with water.

The MQ resins that are suitable for use as component A) in the present invention may contain units D and T, on condition that at least 80 mol % or even 90 mol % of the total siloxane units are units M and Q. The MQ resins may also contain hydroxyl groups. The MQ resins may thus comprise hydroxyl groups in a total weight amount of between 2% and 10% and preferably between 2% and 5%. The MQ resins may also comprise additional end groups, residual hydroxyl groups being, for this purpose, reacted with the groups M.

The component B) is a T propyl resin comprising at least 80 mol % of units $(R^3SiO_{3/2})_c$, $R^3$ being as defined above, i.e. representing an alkyl group containing from 1 to 8 carbon atoms, an aryl group, a carbinol group or an amino group, c being greater than 0, on condition that at least 40 mol % of the groups $R^3$ are propyl groups. Preferably, the T propyl resin according to the invention is a silsesquioxane resin. Silsesquioxane resins are well known in the prior art and are generally obtained by hydrolysis of an organosilane comprising three hydrolysable groups, such as halogen or alkoxy groups, present in the molecule. Component B) may thus be obtained by hydrolysis of propyltrimethoxysilane, propyltriethoxysilane or propyltripropoxysilane, or by cohydrolysis of the above-mentioned propylalkoxysilanes with various alkoxysilanes. Examples of these alkoxysilanes that may be mentioned include methyltrimethoxysilane, methyltriethoxysilane, methyltriisopropoxysilane, dimethyldimethoxysilane and phenyltrimethoxysilane. Propyltrichlorosilane may also be hydrolysed alone, or in the presence of alcohol. In this case, the cohydrolysis may be performed by adding methyltrichlorosilane, dimethyldichlorosilane, phenyltrichlorosilane or similar chlorosilanes and methyltrimethoxysilane, methyltriethoxysilane, methyltriisopropoxysilane or similar methylalkoxysilanes. As alcohols that are suitable for this purpose, mention may be made of methanol, ethanol, n-propyl alcohol, isopropyl alcohol, butanol, methoxyethanol, ethoxyethanol or similar alcohols. As examples of solvents of hydrocarbon type that may be used, mention may be made of toluene, xylene or similar aromatic hydrocarbons; hexane, heptane, isooctane or similar linear or partially branched saturated hydrocarbons; and also cyclohexane or similar aliphatic hydrocarbons.

The T propyl resins as component B) according to the invention may contain units M, D and Q, on condition that at least 80 mol % or even 90 mol % of the total siloxane units are units T. The T propyl resins may also contain hydroxyl groups. Preferably, the T propyl resins comprise between 3% and 8% by weight of hydroxyl groups.

A polyorganosiloxane may also be added to the process according to the invention as component C).

The polyorganosiloxanes that are useful as component C) according to the invention comprise units $R^2{}_2SiO_{2/2}$ or $R^3SiO_{3/2}$. The polyorganosiloxane may be added to introduce various units D and T into the MQ-T propyl resins, so as to modify the properties of the resulting resins. The structure or the formula of the polyorganosiloxane is not limiting, on condition that the said polyorganosiloxane comprises a measurable amount of units $R^2{}_2SiO_{2/2}$ or $R^3SiO_{3/2}$, and that the total amount of polyorganosiloxane added to the reaction between A) and B) does not amount to more than 50 mol % of units D or T in the reaction mixture.

The polyorganosiloxane may comprise combinations of units M, D, T and Q, provided that at least the units D or T are present. Thus, the polyorganosiloxane may be chosen from fluid silicones, gums or resins known in the prior art and comprising units D or T, or mixtures thereof. The units D typically comprise methyl or phenyl groups or mixtures thereof as groups $R^2$. The units T typically comprise methyl or phenyl groups or mixtures thereof as groups $R^3$. The polyorganosiloxane may be a linear fluid polydiorganosiloxane with a viscosity of between 10 and 1000 cS (mm$^2$/s). The fluid polydiorganosiloxane may be a polydimethylsiloxane or a polymethylphenylsiloxane. The polyorganosiloxane may also be an organosilsesquioxane resin. The organosilsesquioxane resin is typically a methylsilsesquioxane resin or a phenylsilsesquioxane resin.

The components A), B) and optionally C) may react via any method known in the prior art for acting on the units M, D, T and Q. Preferably, however, the components A), B) and optionally C) react via a condensation reaction in the presence of a catalyst. The MQ resin is typically present in an aromatic hydrocarbon-based solvent or siloxane solvent. Condensation reaction catalysts that may be used are especially metal hydroxides such as potassium hydroxide or sodium hydroxide; metal salts such as silanolates, carboxylates and carbonates; amines; titanates such as tetrabutyl titanate; and mixtures thereof. Typically, the reaction between the components A), B) and optionally C) is performed by heating the reaction mixture to temperatures ranging from 50 to 140° C. and preferably ranging from 100 to 140° C. The reaction may be performed as a semi-continuous or continuous process or in batch mode.

The mass ratio A/B in the reaction is between 95/5 and 15/85, preferably between 95/5 and 20/80 and preferably between 90/10 and 20/80.

Preferably, the mass ratio A/B is equal to 85/15, or 50/50, or 30/70, or 95/5. Preferably, the mass ratio A/B is equal to 30/70.

The amount of component C) may vary, but on condition that it results in a content of less than 30 mol % of additional units D or T, relative to the total molar amount of siloxane units in the reaction mixture.

Preferably, the siloxane resin is present in the composition in a total solids content of resin ranging from 1% to 80% by weight relative to the total weight of the composition, preferably ranging from 5% to 70% by weight and better still ranging from 6% to 60% by weight.

According to a first embodiment, the composition according to the invention is liquid.

According to a second embodiment, the composition according to the invention is solid.

The term "solid" characterizes the state of the composition at room temperature (25° C.) and at atmospheric pressure (760 mmHg).

Preferably, the composition according to the invention has, when it is solid, a hardness of between 30 and 300 g, or even from 50 to 200 g.

Protocol for Measuring the Hardness:

The measurement is performed according to the following protocol:

A sample of the composition under consideration is hot-cast into a stick mould 12.7 mm in diameter. The mould is then cooled in a freezer for about one hour. The stick of lipstick is then stored at 20° C.

The hardness of the samples is measured after an interval of 24 hours.

The hardness of the samples of compositions of the invention, expressed in grams, is measured using a DFGS2 tensile testing machine sold by the company Indelco-Chatillon.

The hardness corresponds to the maximum shear force exerted by a rigid tungsten wire 250 μm in diameter, advancing at a rate of 100 mm/minute.

The technique described above is usually referred to as the "cheese wire" method.

Preferably, the composition according to the invention comprises less than 3% and better still less than 1% by weight of water relative to the total weight of the composition. More preferably, the composition is totally anhydrous. The term "anhydrous" especially means that water is preferably not deliberately added to the composition, but may be present in trace amount in the various compounds used in the composition.

According to another aspect, the present invention relates to a makeup and/or care process in which the composition as defined previously is applied to keratin materials, and especially to the lips.

Phenyl Silicone Oil

The composition according to the invention comprises at least one phenyl silicone oil (also known as a phenyl silicone). The term "phenyl silicone" means an organopolysiloxane substituted with at least one phenyl group.

The phenyl silicone is preferably non-volatile. The term "non-volatile" refers to an oil whose vapour pressure at room temperature and atmospheric pressure is non-zero and less than 0.02 mm Hg (2.66 Pa) and better still less than $10^{-3}$ mm Hg (0.13 Pa).

Preferably, the weight-average molecular weight of the phenyl silicone oil is between 500 and 10 000 g/mol.

The silicone oil may be chosen from phenyl trimethicones, phenyl dimethicones, phenyl-trimethylsiloxydiphenylsiloxanes, diphenyl dimethicones, diphenyl methyldiphenyl trisiloxanes and 2-phenylethyl trimethylsiloxysilicates.

The silicone oil may correspond to the formula:

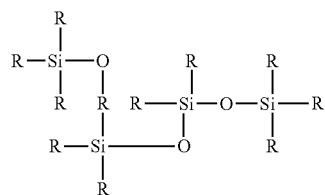

in which the groups R represent, independently of each other, a methyl or a phenyl. Preferably, in this formula, the silicone oil comprises at least three phenyl groups, for example at least four, at least five or at least six.

According to another embodiment, the silicone oil corresponds to the formula:

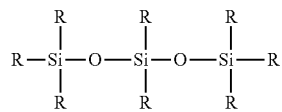

in which the groups R represent, independently of each other, a methyl or a phenyl. Preferably, in this formula, the said organopolysiloxane comprises at least three phenyl groups, for example at least four or at least five.

Mixtures of the phenyl organopolysiloxanes described previously may be used.

Examples that may be mentioned include mixtures of triphenyl, tetraphenyl or pentaphenyl organopolysiloxanes.

According to another embodiment, the silicone oil corresponds to the formula:

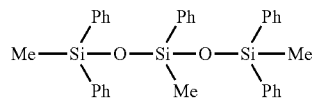

in which Me represents methyl, Ph represents phenyl. Such a phenyl silicone is especially manufactured by Dow Corning under the reference Dow Corning 555 Cosmetic Fluid (INCI name: trimethyl pentaphenyl trisiloxane). The reference Dow Corning 554 Cosmetic Fluid may also be used.

According to another embodiment, the silicone oil corresponds to the formula:

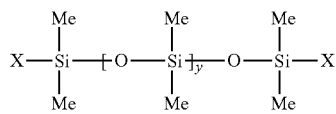

in which Me represents methyl, y is between 1 and 1000 and X represents —CH$_2$—CH(CH$_3$)(Ph).

According to another embodiment, the silicone oil corresponds to the formula:

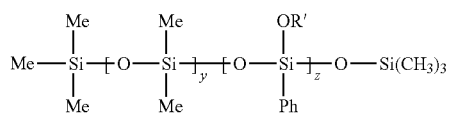

in which —OR' represents —O—SiMe$_3$, y is between 1 and 1000 and z is between 1 and 1000.

The phenyl silicone oil may be chosen from the phenyl silicones of formula (VI) below:

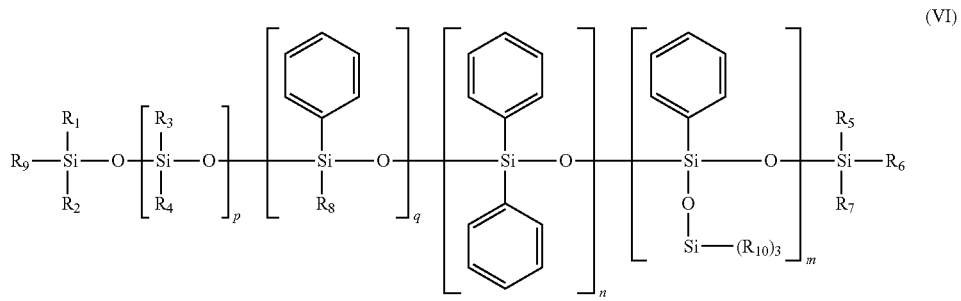

in which

R1 to R10, independently of each other, are saturated or unsaturated, linear, cyclic or branched C1-C30 hydrocarbon-based radicals, m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900, and better still between 1 and 800. Preferably, q is equal to 0.

The phenyl silicone oil may be chosen from the phenyl silicones of formula (VII) below:

in which

R1 to R6, independently of each other, are saturated or unsaturated, linear, cyclic or branched C1-C30 hydrocarbon-based radicals, m, n and p are, independently of each other, integers between 0 and 100, with the proviso that the sum n+m is between 1 and 100.

Preferably, R1 to R6, independently of each other, represent a saturated, linear or branched C1-C30 and especially C1-C12 hydrocarbon-based radical and in particular a methyl, ethyl, propyl or butyl radical.

R1 to R6 may especially be identical, and in addition may be a methyl radical.

Preferably, the value m=1 or 2 or 3, and/or n=0 and/or p=0 or 1 may apply, in formula (VII).

A phenyl silicone oil of formula (VI) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt) may be used.

As phenyl silicone oil of formula (VII), it is especially possible to use phenyl trimethicones such as DC556 from Dow Corning (22.5 cSt), the oil Silbione 70663V30 from Rhône Poulenc (28 cSt) or diphenyl dimethicones such as Belsil oils, especially Belsil PDM1000 (1000 cSt), Belsil PDM 200 (200 cSt) and Belsil PDM 20 (20 cSt) from Wacker. The values in parentheses represent the viscosities at 25° C.

The non-volatile silicone oil may be chosen from the silicones of formula:

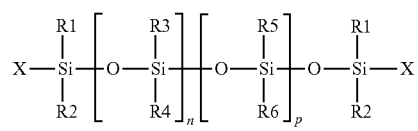

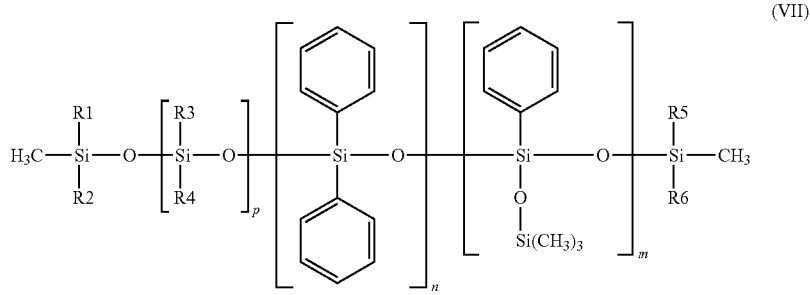

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms or an aryl radical, X is an alkyl radical containing from 1 to 6 carbon atoms, a hydroxyl radical or a vinyl radical, n and p being chosen so as to give the oil a weight-average molecular mass of less than 200 000 g/mol, preferably less than 150 000 g/mol and more preferably less than 100 000 g/mol.

The phenyl silicone oil may especially improve the staying power of the composition without reducing its level of gloss.

The phenyl silicone oil may be present in the composition in a total content ranging from 0.5% to 70% by weight, preferably ranging from 5% to 50% by weight and better still ranging from 5% to 40% by weight relative to the total weight of the composition.

Additional Polymer:

The compositions according to the invention may contain an additional film-forming or non-film-forming polymer.

In the present invention, the term "film-forming polymer" means a polymer that is capable, by itself or in the presence of an auxiliary film-forming agent, of forming a macroscopically continuous film that adheres to keratin materials, and preferably a cohesive film, better still a film whose cohesion and mechanical properties are such that the said film can be isolated and manipulated individually, for example when the said film is prepared by pouring onto a non-stick surface such as a Teflon-coated or silicone-coated surface.

The composition may comprise an aqueous phase and the additional polymer may be present in this aqueous phase. In this case, the polymer will preferably be a polymer in dispersion or an amphiphilic or associative polymer.

The term "polymer in dispersion" means the water-insoluble polymers present in the form of particles of variable size. The polymer may or may not be crosslinked. The size of the polymer particles is typically between 25 and 500 nanometers and preferably between 50 and 200 nanometers. The following polymers in aqueous dispersion may be used: Ultrasol 2075 from Ganz Chemical, Daitosol 5000 AD from Daito Kasei, Avalure UR 450 from Noveon, DynamX from National Starch, Syntran 5760 from Interpolymer, Acusol OP 301 and from Rohm & Haas, and Neocryl A 1090 from Avecia.

The acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Soltex OPT by the company Rohm & Haas, aqueous dispersions of acrylic or styrene/acrylic polymers sold under the brand name Joncryl® by the company Johnson Polymer, or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ® by the company Eastman Chemical Products, and vinyl dispersions, for instance Mexomer PAM® from the company Chimex, and mixtures thereof, are other examples of aqueous dispersions of water-dispersible film-forming polymer particles.

The term "amphiphilic or associative polymers" means polymers comprising one or more hydrophilic parts that make them partially water-soluble and one or more hydrophobic parts via which the polymers associate or interact. The following associative polymers may be used: Nuvis FX 1100 from Elementis, Aculyn 22, Aculyn 44 and Aculyn 46 from Rohm & Haas, Viscophobe DB 1000 from Amerchol. Diblock copolymers formed from a hydrophilic block (polyacrylate or polyethylene glycol) and from a hydrophobic block (polystyrene or polysiloxane) may also be used.

Polymers that are soluble in an aqueous phase containing monodisperse particles may be avoided, since they may cause aggregation of the monodisperse particles. The film-forming polymer may thus be insoluble in such an aqueous phase.

The composition may comprise an oily phase and the film-forming polymer may be present in this oily phase. The polymer may then be in dispersion or in solution. The polymers of type NAD (non-aqueous dispersion) or microgels (for example KSG) may be used, as may polymers of the type PS-PA or styrene-based copolymers (Kraton, Regalite).

As examples of lipodispersible non-aqueous film-forming polymer dispersions in the form of non-aqueous dispersions of polymer particles in one or more silicone and/or hydrocarbon-based oils, which may be surface-stabilized with at least one stabilizer, especially a block, grafted or random polymer, mention may be made of acrylic dispersions in isododecane, for instance Mexomer PAP® from the company Chimex, and dispersions of particles of a grafted ethylenic polymer, preferably an acrylic polymer, in a liquid fatty phase, the ethylenic polymer advantageously being dispersed in the absence of additional stabilizer at the surface of the particles as described especially in document WO 04/055 081.

Among the film-forming polymers that may be used in the composition of the present invention, mention may be made of synthetic polymers, of free-radical type or of polycondensate type, and polymers of natural origin, and mixtures thereof.

The expression "free-radical film-forming polymer" means a polymer obtained by polymerization of unsaturated and especially ethylenically unsaturated monomers, each monomer being capable of homopolymerizing (unlike polycondensates).

The film-forming polymers of free-radical type may be, in particular, vinyl polymers or copolymers, in particular acrylic polymers.

The vinyl film-forming polymers may result from the polymerization of ethylenically unsaturated monomers containing at least one acidic group and/or esters of these acidic monomers and/or amides of these acidic monomers.

Monomers bearing an acidic group which may be used are $\alpha,\beta$-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

Among the alkyl (meth)acrylates that may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates that may be mentioned are hydroxyethyl acrylate, 2-hydroxypropyl acrylate, hydroxyethyl methacrylate and 2-hydroxypropyl methacrylate.

Among the aryl (meth)acrylates that may be mentioned are benzyl acrylate and phenyl acrylate.

The (meth)acrylic acid esters that are particularly preferred are the alkyl (meth)acrylates.

According to the present invention, the alkyl group of the esters may be either fluorinated or perfluorinated, i.e. some or all of the hydrogen atoms of the alkyl group are substituted with fluorine atoms.

Examples of amides of the acid monomers that may be mentioned are (meth)acrylamides, and especially N-alkyl (meth)acrylamides, in particular of a $C_2$-$C_{12}$ alkyl. Among the N-alkyl(meth)acrylamides that may be mentioned are N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. In particular, these monomers may be polymerized with acid monomers and/or esters thereof and/or amides thereof, such as those mentioned above.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and α-methylstyrene.

Among the film-forming polycondensates that may be mentioned are polyurethanes, polyesters, polyesteramides, polyamides, epoxyester resins and polyureas.

The polyurethanes may be chosen from anionic, cationic, nonionic and amphoteric polyurethanes, polyurethane-acrylics, polyurethane-polyvinyl-pyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, in particular diols.

The dicarboxylic acid may be aliphatic, alicyclic or aromatic. Examples of such acids that may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalene-dicarboxylic acid or 2,6-naphthalene-dicarboxylic acid. These dicarboxylic acid monomers may be used alone or as a combination of at least two dicarboxylic acid monomers. Among these monomers, the ones preferentially chosen are phthalic acid, isophthalic acid and terephthalic acid.

The diol may be chosen from aliphatic, alicyclic and aromatic diols. The diol used is preferably chosen from: ethylene glycol, diethylene glycol, triethylene glycol, 1,3-propanediol, cyclohexanedimethanol and 4-butanediol. Other polyols that may be used are glycerol, pentaerythritol, sorbitol and trimethylol-propane.

The polyesteramides may be obtained in a manner analogous to that of the polyesters, by polycondensation of diacids with diamines or amino alcohols. Diamines that may be used are ethylenediamine, hexamethylenediamine and meta- or para-phenylenediamine. An amino alcohol that may be used is monoethanolamine.

The polyester may also comprise at least one monomer bearing at least one group —$SO_3M$, with M representing a hydrogen atom, an ammonium ion $NH_4^+$ or a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may be used in particular.

The aromatic nucleus of the difunctional aromatic monomer also bearing a group —$SO_3M$ as described above may be chosen, for example, from benzene, naphthalene, anthracene, biphenyl, oxybiphenyl, sulfonylbiphenyl and methylenebiphenyl nuclei. As examples of difunctional aromatic monomers also bearing a group —$SO_3M$, mention may be made of: sulfoisophthalic acid, sulfoterephthalic acid, sulfophthalic acid, 4-sulfonaphthalene-2,7-dicarboxylic acid.

According to one example of a composition according to the invention, the film-forming polymer may be a polymer dissolved in a liquid fatty phase comprising organic solvents or oils (the film-forming polymer is thus said to be a liposoluble polymer). The liquid fatty phase preferably comprises a volatile oil, optionally mixed with a non-volatile oil.

Examples of liposoluble polymers that may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octane-dioate, divinyl dodecanedioate and divinyl octadecane-dioate.

Examples of these copolymers that may be mentioned are the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Examples of liposoluble film-forming polymers that may be mentioned include copolymers of a vinyl ester and of at least one other monomer that may be a vinyl ester, especially vinyl neodecanoate, vinyl benzoate and vinyl t-butylbenzoate, an α-olefin, an alkyl vinyl ether or an allylic or methallylic ester.

Examples of liposoluble film-forming polymers that may also be mentioned are liposoluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such liposoluble copolymers may be chosen from copolymers of polyvinyl stearate, polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly(meth)acrylates to be crosslinked with the aid of ethylene glycol dimethacrylate or tetraethylene glycol dimethacrylate.

The liposoluble copolymers defined above are known and are described in particular in patent application FR-A-2 232 303; they may have a weight-average molecular weight ranging from 2000 to 500 000 and preferably from 4000 to 200 000.

As liposoluble film-forming polymers that may be used in the invention, mention may also be made of polyalkylenes and in particular copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) and in particular copolymers of vinylpyrrolidone and of $C_2$ to $C_{40}$ and better still $C_3$ to $C_{20}$ alkene. As examples of VP copolymers which may be used in the invention, mention may be made of the copolymers of VP/vinyl acetate, VP/ethyl methacrylate, butylated polyvinyl-pyrrolidone (PVP), VP/ethyl methacrylate/methacrylic acid, VP/eicosene, VP/hexadecene, VP/triacontene, VP/styrene or VP/acrylic acid/lauryl methacrylate.

Mention may also be made of silicone resins, which are generally soluble or swellable in silicone oils, which are crosslinked polyorganosiloxane polymers. The nomenclature of silicone resins is known under the name "MDTQ", the resin being described as a function of the various siloxane monomer units it comprises, each of the letters "MDTQ" characterizing a type of unit.

Examples of commercially available polymethylsilsesquioxane resins that may be mentioned include those sold by the company Wacker under the reference Resin MK, such as Belsil PMS MK, or by the company Shin-Etsu under the reference KR-220L.

Examples of commercially available polypropyl-silsesquioxane resins that may be mentioned include those sold under the reference DC670 by the company Dow Corning.

Siloxysilicate resins that may be mentioned include trimethyl siloxysilicate (TMS) resins such as those sold under the reference SR 1000 by the company General Electric or under the reference TMS 803 by the company Wacker. Mention may also be made of the trimethyl siloxysilicate resins sold in a solvent such as cyclomethicone, sold under the name KF-7312J by the company Shin-Etsu, and DC 749 and DC 593 by the company Dow Corning.

In the case of skin makeup or care compositions, the combination of a resin according to the invention with a trimethyl siloxysilicate resin or a polypropylsilsesquioxane resin makes it possible to improve the durability of the transfer resistance.

Mention may also be made of silicone resin copolymers such as those mentioned above with polydimethylsiloxanes, for instance the pressure-sensitive adhesive copolymers sold by the company Dow Corning under the reference Bio-PSA and described in document U.S. Pat. No. 5,162,410, or the silicone copolymers derived from the reaction of a silicone resin, such as those described above, and of a diorganosiloxane, as described in document WO 2004/073 626.

According to one embodiment of the invention, the film-forming polymer is a film-forming block ethylenic polymer (which is preferably essentially linear), which preferably comprises at least a first block and at least a second block with different glass transition temperatures (Tg), the said first and second blocks being linked together via an intermediate block comprising at least one constituent monomer of the first block and at least one constituent monomer of the second block.

Advantageously, the first and second blocks of the block polymer are mutually incompatible.

Such polymers are described, for example, in documents EP 1 411 069 or WO 04/028 488.

Preferably, according to this embodiment, the block ethylenic polymer, comprising at least a first block and at least a second block, is characterized in that the first block is obtained from at least one acrylate monomer of formula $CH_2=CH-COOR_2$ in which $R_2$ represents a $C_4$ to $C_{12}$ cycloalkyl group and at least one methacrylate monomer of formula $CH_2=C(CH_3)-COOR_2$ in which $R'_2$ represents a $C_4$ to $C_{12}$ cycloalkyl group, and characterized in that the second block is obtained from an acrylic acid monomer and from at least one monomer with a glass transition temperature of less than or equal to 20° C. Such polymers and the process for preparing them are described, for example, in document EP 1 882 709.

The film-forming polymer may be chosen from block or random polymers and/or copolymers especially comprising polyurethanes, polyacrylics, silicones, fluoro polymers, butyl rubbers, ethylene copolymers, natural gums and polyvinyl alcohols, and mixtures thereof. The monomers of the block or random copolymers comprising at least one combination of monomers whose resulting polymer has a glass transition temperature of less than room temperature (25° C.) may be chosen especially from butadiene, ethylene, propylene, acrylic, methacrylic, isoprene, isobutene and a silicone, and mixtures thereof.

The film-forming polymer may also be present in the first and/or second composition in the form of particles dispersed in an aqueous phase or in a non-aqueous solvent phase, which is generally known as a latex or pseudolatex. The techniques for preparing these dispersions are well known to those skilled in the art.

The composition according to the invention may comprise a plasticizer that promotes the formation of a film with the film-forming polymer. Such a plasticizer may be chosen from any compound known to those skilled in the art as being capable of satisfying the desired function.

As other examples of film-forming systems that may be used in the compositions according to the invention, mention may be made of systems in which the film is formed in situ at the time of application of the composition or of a mixture of compositions containing two silicone compounds that react together when they are placed in contact. Such systems are described especially in patent application WO 2007/071 706, the content of which is incorporated herein by reference. Systems of this type are also described in patent applications US 2007/142 575 and US 2007/142 599, the content of which is also incorporated herein by reference.

Other Polymers:

The compositions according to the invention may contain an elastomer, especially a polyglycerolated silicone elastomer. By way of example, use is made of an elastomeric crosslinked organopolysiloxane that may be obtained by a crosslinking addition reaction of a diorganopolysiloxane containing at least one hydrogen bonded to silicon and of polyglycerolated compounds containing ethylenically unsaturated groups, especially in the presence of a platinum catalyst.

Polyglycerolated silicone elastomers that may be used include those sold under the names KSG-710, KSG-810, KSG-820, KSG-830 and KSG-840 by the company Shin-Etsu.

The compositions according to the invention may also comprise an additional emulsifying silicone elastomer.

By way of example, use may be made of polyoxyalkylenated elastomers as described especially in U.S. Pat. No. 5,236,986, U.S. Pat. No. 5,412,004, U.S. Pat. No. 5,837,793 and U.S. Pat. No. 5,811,487, the content of which is incorporated by reference.

Polyoxyalkylenated silicone elastomers that may be used include those sold under the names KSG-21, KSG-20, KSG-30, KSG-31, KSG-32, KSG-33, KSG-210, KSG-310, KSG-320, KSG-330, KSG-340 and X-226146 by the company Shin-Etsu, and DC9010 and DC9011 by the company Dow Corning.

When they are in combination with the resins according to the invention, these particular elastomers may make it possible to improve the transfer-resistance and comfort (suppleness) properties of the compositions comprising them.

The compositions according to the invention may also comprise a non-emulsifying elastomer.

Non-emulsifying elastomers are especially described in patent applications JP-A-61-194 009, EP-A-242 219, EP-A-285 886 and EP-A-765 656, the content of which is incorporated by reference.

Spherical non-emulsifying elastomers that may be used include those sold under the names DC9040, DC9041, DC9509, DC9505 and DC9506 by the company Dow Corning.

The spherical non-emulsifying silicone elastomer may also be in the form of an elastomeric crosslinked organopolysiloxane powder coated with silicone resin, especially with silsesquioxane resin, as described, for example, in U.S. Pat. No. 5,538,793, the content of which is incorporated by reference. Such elastomers are sold under the names KSP-100, KSP-101, KSP-102, KSP-103, KSP-104 and KSP-105 by the company Shin-Etsu.

Other elastomeric crosslinked organopolysiloxanes in the form of spherical powders may be powders of a hybrid silicone functionalized with fluoroalkyl groups, sold especially under the name KSP-200 by the company Shin-Etsu; powders of a hybrid silicone functionalized with phenyl groups, sold especially under the name KSP-300 by the company Shin-Etsu.

Silicone elastomers bearing a group MQ, such as those sold by the company Wacker under the names Belsil RG100, Belsil RPG33 and, preferentially, RG80, may also be used in the compositions according to the invention. These particular elastomers, when they are in combination with the resins according to the invention, may make it possible to improve the transfer-resistance properties of the compositions comprising them.

The Oils:

The composition according to the invention may comprise at least one oil.

The oil may be chosen from hydrocarbon-based oils, silicone oils and fluoro oils.

The oil may be chosen from volatile oils, non-volatile oils and mixtures thereof.

The term hydrocarbon-based oil means an oil formed essentially from, or even consisting of, carbon and hydrogen atoms, and possibly oxygen and nitrogen atoms, and containing no silicon or fluorine atoms; it may contain ester, ether, amine or amide groups.

The term silicone oil means an oil containing at least one silicon atom, and especially containing Si—O groups.

The term fluoro oil means an oil containing at least one fluorine atom.

The composition according to the invention may comprise at least one volatile oil.

The term "volatile oil" means an oil (or non-aqueous medium) that is capable of evaporating on contact with the skin in less than one hour, at room temperature and atmospheric pressure. The volatile oil is a cosmetic volatile oil, which is liquid at room temperature, having in particular a non-zero vapour pressure, at room temperature and atmospheric pressure, in particular having a vapour pressure ranging from 0.13 Pa to 40 000 Pa ($10^{-3}$ to 300 mmHg), and preferably ranging from 1.3 Pa to 13 000 Pa (0.01 to 100 mmHg) and preferentially ranging from 1.3 Pa to 1300 Pa (0.01 to 10 mmHg).

Furthermore, the volatile oil generally has a boiling point, measured at atmospheric pressure, ranging from 150° C. to 260° C. and preferably ranging from 170° C. to 250° C.

The composition according to the invention may comprise a volatile hydrocarbon-based oil in particular chosen from hydrocarbon-based oils with a flash point ranging from 40° C. to 102° C., preferably ranging from 40° C. to 55° C., and preferentially ranging from 40° C. to 50° C.

As volatile hydrocarbon-based oil, mention may be made of volatile hydrocarbon-based oils containing from to 16 carbon atoms and mixtures thereof, and especially C8-C16 branched alkanes, for instance C8-C16 isoalkanes (also known as isoparaffins), isododecane, isodecane, isohexadecane and for example the oils sold under the trade names Isopar or Permethyl, C8-C16 branched esters such as isohexyl neopentanoate, and mixtures thereof. Preferably, the volatile hydrocarbon-based oil is chosen from volatile hydrocarbon-based oils containing from 8 to 16 carbon atoms, and mixtures thereof, in particular from isododecane, isodecane, isohexadecane and is especially isododecane.

For skin makeup products, especially foundations and lipsticks, linear hydrocarbon-based volatile oils containing from 8 to 16 carbon atoms will advantageously be used.

Volatile silicone oils that may be mentioned include linear or cyclic silicones containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethyl-hexyltrisiloxane, heptamethyloctyltrisiloxane, octamethyltrisiloxane and decamethyltetrasiloxane, and mixtures thereof.

The volatile oil may be present in the composition according to the invention in a content ranging from 0.1% to 90% by weight, preferably ranging from 1% to 70% by weight and preferentially ranging from 5% to 50% by weight relative to the total weight of the composition.

The composition according to the invention may comprise at least one non-volatile oil.

Non-volatile hydrocarbon-based oils that may be used include liquid paraffin (or petroleum jelly), squalane, hydrogenated polyisobutylene (Parleam oil), perhydrosqualene, mink oil, turtle oil, soybean oil, sweet almond oil, beauty-leaf oil, palm oil, grapeseed oil, sesame oil, corn oil, arara oil, rapeseed oil, sunflower oil, cotton oil, apricot oil, castor oil, avocado oil, jojoba oil, olive oil or cereal germ oil; esters of lanolic acid, of oleic acid, of lauric acid or of stearic acid; fatty esters, especially of C12-C36, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl)succinate, diisostearyl malate, and glyceryl or diglyceryl triisostearate; behenic acid, oleic acid, linoleic acid, linolenic acid or isostearic acid; higher fatty alcohols, especially of C16-C22, such as cetanol, oleyl alcohol, linoleyl alcohol or linolenyl alcohol, isostearyl alcohol or octyldodecanol; and mixtures thereof.

The non-volatile oil may be present in a content ranging from 0.1% to 70% by weight, preferably ranging from 0.5% to 60% by weight and preferentially ranging from 1% to 50% by weight relative to the total weight of the non-volatile liquid fatty phase.

Structuring Agents:

The composition according to the invention may comprise a structuring agent.

The term "structuring agent" means a compound capable of increasing the viscosity of the composition. The structuring agent makes it possible especially to obtain a composition that can have a texture ranging from fluid to solid textures.

The structuring agent may be present in the composition in a content ranging from 0.05% to 40% by weight, preferably ranging from 0.1% to 30% by weight and preferentially ranging from 0.1% to 25% by weight, relative to the total weight of the composition.

The structuring agent may be chosen especially from thickeners (oily-medium thickeners; aqueous-medium thickeners), organogelling agents, waxes, pasty compounds and gums.

The aqueous-medium thickener may be chosen from:
hydrophilic clays,
hydrophilic fumed silica,
water-soluble cellulose-based thickeners,
guar gum, xanthan gum, carob gum, scleroglucan gum, gellan gum, rhamsan gum, karaya gum or carrageenan gum,
alginates, maltodextrins, starch and its derivatives, and hyaluronic acid and its salts,
the polyglyceryl (meth)acrylate polymers sold under the names "Hispagel" or "Lubragel" by the companies Hispano Quimica or Guardian,
polyvinylpyrrolidone,
polyvinyl alcohol,
crosslinked acrylamide polymers and copolymers, such as those sold under the names PAS 5161 or Bozepol C by the company Hoechst, Sepigel 305 by the company SEPPIC by the company Allied Colloid, or alternatively
the crosslinked methacryloyloxyethyltrimethylammonium chloride homopolymers sold under the name "Salcare SC95" by the company Allied Colloid,
associative polymers and especially associative polyurethanes.

Such thickeners are described especially in patent application EP-A-1 400 234, the content of which is incorporated by reference.

The oily-medium thickener may be chosen from:
carboxylate silicones,
saccharide silicones,
organophilic clays;
hydrophobic fumed silicas;
alkyl guar gums (with a $C_1$-$C_6$ alkyl group), such as those described in EP-A-708 114;
hydrophobic celluloses,
oil-gelling polymers, for instance triblock polymers or star polymers resulting from the polymerization or copolymerization of at least one monomer containing an ethylenic group, for instance the polymers sold under the name Kraton;
polymers with a weight-average molecular mass of less than 100 000, comprising a) a polymer skeleton containing hydrocarbon-based repeating units containing at least one heteroatom, and optionally b) at least one pendent fatty chain and/or at least one terminal fatty chain, which are optionally functionalized, containing from 6 to 120 carbon atoms and being linked to these hydrocarbon-based units, as described in patent applications WO-A-02/056847 and WO-A-02/47619, the content of which is incorporated by reference; in particular, polyamide resins (especially comprising alkyl groups containing from 12 to 22 carbon atoms) such as those described in U.S. Pat. No. 5,783,657, the content of which is incorporated by reference;

the silicone-based polyamide resins as described in patent application EP-A-1 266 647 and in the French patent application filed under the number 0 216 039, the content of which is incorporated by reference.

Such thickeners are especially described in patent application EP-A-1 400 234, the content of which is incorporated by reference.

The organogelling agents may be chosen from those described in patent application WO-A-03/105 788, the content of which is incorporated by reference.

In particular, it may be advantageous to combine the resins according to the invention with particular organogelling agents, and especially:

the bis-urea derivatives of general formula (I):

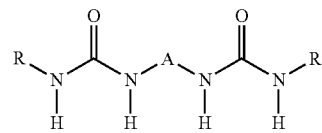

in which:
A is a group of formula:

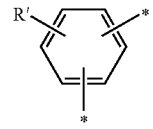

with R' being a linear or branched $C_1$ to $C_4$ alkyl radical and the *s symbolizing the points of attachment of the group A to each of the two nitrogen atoms of the rest of the compound of general formula (I), and R is a saturated or unsaturated, non-cyclic, mono-branched $C_6$ to $C_{15}$ alkyl radical whose hydrocarbon-based chain is optionally interrupted with 1 to 3 heteroatoms chosen from O, S and N, or a salt or isomer thereof, described especially in patent application FR-A-2 892 303, the silicone bis-urea derivatives of general formula (I), or a salt and/or isomer thereof:

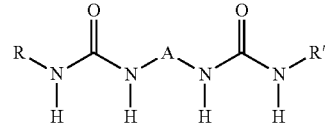

in which:

A is a group of formula (II):

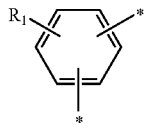

with $R_1$ being a linear or branched $C_1$-$C_4$ alkyl radical, and the *s symbolizing the points of attachment of the group A to each of the two nitrogen atoms of the rest of the compound of general formula (I), and R and R', which may be identical or different, are chosen from:

i) the radicals of formula (III):

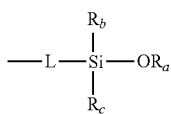

in which:

L is a single bond or a divalent carbon-based radical, especially a linear, branched and/or cyclic, saturated or unsaturated hydrocarbon-based radical (alkylene), containing 1 to 18 carbon atoms, and possibly comprising 1 to 4 heteroatoms chosen from N, O and S;

$R_a$ is:
a) a carbon-based radical, especially a linear, branched and/or cyclic, saturated or unsaturated hydrocarbon-based radical (alkyl), containing 1 to 18 carbon atoms, and possibly comprising 1 to 8 heteroatoms chosen from N, O, Si and S; or
b) a silicone radical of formula:

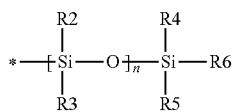

with n being between 0 and 100, especially between 1 and 80, or even 2 to 20;

and $R_2$ to $R_6$ being, independently of each other, carbon-based radicals, especially linear or branched hydrocarbon-based radicals (alkyl) containing 1 to 12 and especially 1 to 6 carbon atoms, and possibly comprising 1 to 4 heteroatoms, especially O;

$R_b$ and $R_c$ are, independently of each other, chosen from:
a) carbon-based radicals, especially linear, branched and/ or cyclic, saturated or unsaturated hydrocarbon-based radicals (alkyl), containing 1 to 18 carbon atoms, and possibly comprising 1 to 4 heteroatoms chosen from N, O, Si and S;
b) the radicals of formula:

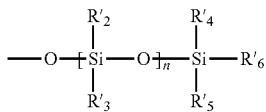

with n being between 0 and 100, especially between 1 and 80, or even 2 to 20;

and $R'_2$ to $R'_6$ being, independently of each other, carbon-based radicals, especially linear or branched hydrocarbon-based radicals (alkyl), containing 1 to 12 and especially 1 to 6 carbon atoms, and possibly comprising 1 to 4 heteroatoms, especially O;

and ii) linear, branched and/or cyclic, saturated or unsaturated $C_1$-$C_{30}$ alkyl radicals, optionally comprising 1 to 3 heteroatoms chosen from O, S, F and N;

it being understood that at least one of the radicals R and/or R' is of formula (III), such as those described in patent application FR-A-2 900 819, the bis-urea derivatives described in patent application FR-A-2 899 4476.

Wax(es)

The composition may comprise at least one solid fatty substance chosen from waxes, as structuring agent.

The wax under consideration in the context of the present invention is generally a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for the invention may have a melting point of greater than or equal to 45° C. and in particular greater than or equal to 55° C.

For the purposes of the invention, the melting point corresponds to the temperature of the most endothermic peak observed by thermal analysis (DSC) as described in standard ISO 11357-3; 1999. The melting point of the wax may be measured using a differential scanning calorimeter (DSC), for example the calorimeter sold under the name MDSC 2920 by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in absorbed power as a function of the temperature.

The waxes that may be used in the compositions according to the invention are chosen from waxes that are solid at room temperature of animal, plant, mineral or synthetic origin, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Among these waxes that may especially be mentioned are isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylol-propane) tetrastearate sold under the name Hest 2T-4S® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

A wax that may be used is a $C_{20}$-$C_{40}$ alkyl (hydroxystearyloxy)stearate (the alkyl group containing from 20 to 40 carbon atoms), alone or as a mixture.

Such a wax is especially sold under the names Kester Wax K 82 P®, Hydroxypolyester K 82 P®, Kester Wax K 80 P® and Kester Wax K 82 H® by the company Koster Keunen.

As microwaxes that may be used in the compositions according to the invention, mention may be made especially of carnauba microwaxes, such as the product sold under the name MicroCare 350® by the company Micro Powders, synthetic microwaxes, such as the product sold under the name MicroEase 114S® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

The composition according to the invention may have a wax content ranging from 0.1% to 50% by weight and better still from 1% to 30% by weight relative to the total weight of the composition.

Pasty Compounds

The composition according to the invention may comprise at least one pasty compound as structuring agent. Pasty fatty substances are considered as solid fatty substances for the purposes of the present invention.

For the purposes of the present invention, the term "pasty" means a lipophilic fatty compound that undergoes a reversible solid/liquid change of state and that comprises in the solid state an anisotropic crystal organization, and comprises, at a temperature of 23° C., a liquid fraction and a solid fraction.

In other words, the starting melting point of the pasty compound is less than 23° C. The liquid fraction of the pasty compound measured at 23° C. may represent 9% to 97% by weight of the compound. This liquid fraction at 23° C. preferably represents between 15% and 85% and more preferably between 40% and 85% by weight.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound to change from the solid state to the liquid state. The pasty compound is said to be in the solid state when all of its mass is in solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5 or 10° C. per minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., constituted of a liquid fraction and a solid fraction.

The liquid fraction of the pasty compound, measured at 32° C., preferably represents from 30% to 100% by weight of the compound, preferably from 50% to 100% and more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same manner as the heat of fusion consumed at 23° C.

The pasty compound is preferably chosen from synthetic compounds and compounds of plant origin. A pasty compound may be obtained by synthesis from starting materials of plant origin.

The pasty compound may advantageously be chosen from:
i) lanolin and derivatives thereof,
ii) polymer or non-polymer silicone compounds,
iii) polymer or non-polymer fluoro compounds,
iv) vinyl polymers, especially:
v) olefin homopolymers
vi) olefin copolymers
vii) hydrogenated diene homopolymers and copolymers
viii) linear or branched oligomers, which are homopolymers or copolymers of alkyl (meth)acrylates preferably containing a $C_8$-$C_{30}$ alkyl group
ix) oligomers, which are homopolymers and copolymers of vinyl esters containing $C_8$-$C_{30}$ alkyl groups
x) oligomers, which are homopolymers and copolymers of vinyl ethers containing $C_8$-$C_{30}$ alkyl groups,
xi) liposoluble polyethers resulting from the polyetherification between one or more $C_2$-$C_{100}$ and preferably $C_2$-$C_{50}$ diols,
xii) esters,
xiii) and mixtures thereof.
Among the esters that are especially preferred are:
xiv) esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as the product sold under the brand name Softisan 649 by the company Sasol,
xv) arachidyl propionate sold under the brand name Waxenol 801 by Alzo,
xvi) phytosterol esters,
xvii) fatty acid triglycerides and derivatives thereof,
xviii) pentaerythritol esters,
xix) non-crosslinked polyesters resulting from polycondensation between a linear or branched $C_4$-$C_{50}$ dicarboxylic acid or polycarboxylic acid and a $C_2$-$C_{50}$ diol or polyol,
xx) aliphatic esters of an ester resulting from the esterification of an aliphatic hydroxycarboxylic acid with an aliphatic carboxylic acid, xxi) polyesters resulting from the esterification, with a polycarboxylic acid, of an ester of an aliphatic hydroxycarboxylic acid, the said ester comprising at least two hydroxyl groups, such as the products Risocast DA-H® and Risocast DA-L®, xxii) esters of a diol dimer and of a diacid dimer, where appropriate esterified on their free alcohol or acid function (s) with acid or alcohol radicals, such as Plandool-G, xviii) and mixtures thereof.

Among the pasty compounds of plant origin, a mixture of soybean sterols and of oxyethylenated (5 EO) oxypropylenated (5 PO) pentaerythritol, sold under the reference Lanolide by the company Vevy, will preferably be chosen.

Preferably, the composition comprises a total content of pasty fatty substances ranging from 0.5% to 50% by weight, preferably from 1% to 40% by weight and better still from 5% to 30% by weight relative to the weight of the composition.

The gums are generally polydimethylsiloxanes (PDMS) of high molecular weight or cellulose gums or polysaccharides.

Surfactants

The composition according to the invention may comprise at least one surfactant.

The surfactant may be lipophilic and/or hydrophilic, used alone or in combination.

The surfactant may be chosen from nonionic, anionic, cationic and amphoteric surfactants.

The nonionic surfactant may be chosen from:

a $C_8$-$C_{22}$ alkyl dimethicone copolyol, i.e. an oxypropylenated and/or oxyethylenated polymethyl ($C_8$-$C_{22}$)alkyl dimethyl methyl siloxane.

The $C_8$-$C_{22}$ alkyl dimethicone copolyol is advantageously a compound of formula (I) below:

$$(CH_3)_3Si-O-\left[\begin{array}{c}CH_3\\|\\Si-O\\|\\(CH_2)_p\\|\\CH_3\end{array}\right]_o \left[\begin{array}{c}CH_3\\|\\Si-O\\|\\(CH_2)_q\\|\\O\\|\\PE\end{array}\right]_m \left[\begin{array}{c}CH_3\\|\\Si-O\\|\\CH_3\end{array}\right]_n -Si(CH_3)_3 \quad (I)$$

in which:
PE represents $-(C_2H_4O)_x-(C_3H_6O)_y-$R, R being chosen from a hydrogen atom and an alkyl radical of 1 to 4 carbon atoms, x ranging from 0 to 100 and y ranging from 0 to 80, x and y not simultaneously being 0
m ranging from 1 to 40
n ranging from 10 to 200
o ranging from 1 to 100
p ranging from 7 to 21
q ranging from 0 to 4
and preferably:
R=H
m=1 to 10
n=10 to 100
o=1 to 30
p=15
q=3.

A $C_8$-$C_{22}$ alkyl dimethicone copolyol that may be mentioned is cetyl dimethicone copolyol, for instance the product sold under the name Abil EM-90 by the company Goldschmidt.

a dimethicone copolyol, i.e. an oxypropylenated and/or oxyethylenated polydimethyl methyl siloxane. It contains no alkyl groups with a chain length of more than 8 carbon atoms, especially $C_8$-$C_{22}$.

Dimethicone copolyols that may be used include those corresponding to formula (II) below:

$$R_1-\underset{\underset{CH_3}{|}}{\overset{\overset{CH_3}{|}}{Si}}O-\left[\underset{\underset{CH_3}{|}}{\overset{\overset{CH_3}{|}}{Si}}O\right]_A\left[\underset{\underset{R_2}{|}}{\overset{\overset{CH_3}{|}}{Si}}O\right]_B\underset{\underset{CH_3}{|}}{\overset{\overset{CH_3}{|}}{Si}}-R_3 \quad (II)$$

in which:
$R_1$, $R_2$ and $R_3$, independently of each other, represent a $C_1$-$C_6$ alkyl radical or a radical $-(CH_2)_x-(OCH_2CH_2)_y-(OCH_2CH_2)_z-OR_4$, at least one radical $R_1$, $R_2$ or $R_3$ not being an alkyl radical; $R_4$ being a hydrogen, a $C_1$-$C_3$ alkyl radical or a $C_2$-$C_4$ acyl radical;
A is an integer ranging from 0 to 200;
B is an integer ranging from 0 to 50; on condition that A and B are not simultaneously equal to zero;
x is an integer ranging from 1 to 6;
y is an integer ranging from 1 to 30;
z is an integer ranging from 0 to 5.

According to one preferred embodiment of the invention, in the compound of formula (II), $R_1$=$R_3$=methyl radical, x is an integer ranging from 2 to 6 and y is an integer ranging from 4 to 30. $R_4$ is in particular a hydrogen.

Examples of compounds of formula (II) that may be mentioned include the compounds of formula (III):

$$(CH_3)_3SiO-[(CH_3)_2SiO]_A-(CH_3SiO)_B-Si(CH_3)_3 \\ | \\ (CH_2)_2-(OCH_2CH_2)_y-OH \quad (III)$$

in which A is an integer ranging from 20 to 105, B is an integer ranging from 2 to 10 and y is an integer ranging from 10 to 20.

Examples of silicone compounds of formula (II) that may also be mentioned include the compounds of formula (IV):

$$HO-(CH_2CH_2O)_y-(CH_2)_3-[(CH_3)_2SiO]_{A'}-[(CH_3)_2Si]-(CH_2)_3-(OCH_2CH_2)_y-OH \quad (IV)$$

in which A' and y are integers ranging from 10 to 20.

Dimethicone copolyols that may be used include those sold under the names DC 5329, DC 7439-146, DC 2-5695 and Q4-3667 by the company Dow Corning; KF-6013, KF-6015, KF-6016 and KF-6017 by the company Shin-Etsu.

The compounds DC 5329, DC 7439-146 and DC 2-5695 are compounds of formula (III) in which, respectively, A is 22, B is 2 and y is 12; A is 103, B is 10 and y is 12; A is 27, B is 3 and y is 12.

Nonionic surfactants that may also be mentioned include fatty acid esters of polyols, for instance sorbitol or glyceryl mono-, di-, tri- or sesqui-oleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl)ethers.

Anionic surfactants that may be mentioned include carboxylates (sodium 2-(2-hydroxyalkyloxy)acetate)), amino acid derivatives (N-acylglutamates, N-acylglycinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, and mixtures thereof.

Amphoteric and zwitterionic surfactants that may be used include betaines, N-alkylamidobetaines and derivatives thereof, glycine derivatives, sultaines, alkyl polyaminocarboxylates and alkylamphoacetates, and mixtures thereof.

Such surfactants are described especially in patent application WO-A-02/056 854, the content of which is incorporated by reference.

The surfactant may be present in the composition according to the invention in a content ranging from 0.1% to 10% by weight, preferably ranging from 0.5% to 8% by weight and preferentially ranging from 0.5% to 7% by weight, relative to the total weight of the composition.

Dyestuffs:

The composition according to the invention may comprise at least one dyestuff.

The dyestuff may be chosen from pulverulent dyestuffs (especially pigments and nacres) and water-soluble dyestuffs.

The term "pigments" should be understood as meaning white or coloured, mineral or organic particles of any form, which are insoluble in the physiological medium, and which are intended to colour the composition.

The term "nacres" should be understood as meaning iridescent particles of any form, produced especially by certain molluscs in their shell, or else synthesized.

The pigments may be white or coloured, and mineral and/or organic. Among the mineral pigments that may be mentioned are titanium dioxide, optionally surface-treated, zirconium oxide or cerium oxide, and also zinc oxide, iron oxide (black, yellow or red) or chromium oxide, manganese violet, ultramarine blue, chromium hydrate and ferric blue, and metal powders, for instance aluminium powder or copper powder.

Among the organic pigments that may be mentioned are carbon black, pigments of D & C type, and lakes based on cochineal carmine or on barium, strontium, calcium or aluminium.

Mention may also be made of pigments with an effect, such as particles comprising a natural or synthetic, organic or mineral substrate, for example glass, acrylic resins, polyester, polyurethane, polyethylene terephthalate, ceramics or aluminas, the said substrate being uncoated or coated with metallic substances, for instance aluminium, gold, silver, platinum, copper or bronze, or with metal oxides, for instance titanium dioxide, iron oxide or chromium oxide, and mixtures thereof.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment of the abovementioned type, and also nacreous pigments based on bismuth oxychloride. Interference pigments, especially liquid-crystal or multilayer interference pigments, may also be used.

The term "alkyl" mentioned in the compounds cited above especially denotes an alkyl group containing from 1 to 30 carbon atoms and preferably containing from 5 to 16 carbon atoms.

Hydrophobic-treated pigments are described especially in patent application EP-A-1 086 683.

The water-soluble dyes are, for example, beetroot juice or methylene blue.

The synthetic or natural liposoluble dyes are, for example, DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, annatto and curcumin.

The dyestuffs, in particular the pigments treated with a hydrophobic agent, may be present in the composition in a content ranging from 0.1% to 50% by weight, preferably ranging from 0.5% to 30% by weight and preferentially ranging from 1% to 20% by weight, relative to the total weight of the composition.

Fillers:

The composition according to the invention may comprise at least one filler.

For the purposes of the present invention, the term "filler" denotes solid particles of any form, which are in an insoluble form and dispersed in the medium of the composition, even at temperatures that may be up to the melting point of all the fatty substances of the composition.

Generally, the fillers used according to the invention are colourless or white, namely non-pigmentary, i.e. they are not used to give a particular colour or shade to the composition according to the invention, even though their use may inherently lead to such a result. These fillers serve especially to modify the rheology or texture of the composition.

In this respect, they are different from nacres, organic pigmentary materials, for instance carbon black, pigments of D&C type, and lakes based on cochineal carmine or on barium, strontium, calcium or aluminium, and inorganic pigmentary materials, for instance titanium dioxide, zirconium oxide or cerium oxide, and also iron oxides (black, yellow or red), chromium oxide, manganese violet, ultramarine blue, chromium hydrate and ferric blue, which are, themselves, used to give a shade and coloration to the compositions incorporating them.

For the purposes of the invention, such compounds are not covered by the definition of fillers, which thus covers non-pigmentary fillers, which may be organic or inorganic.

The non-pigmentary fillers used in the compositions according to the present invention may be of lamellar, globular or spherical form, of fibre type, or of any intermediate form between these defined forms.

The size of the particles, i.e. their granulometry, is chosen so as to ensure the good dispersion of the fillers in the composition according to the invention. The granulometry of the particles may be distributed within the range from 5 μm to 10 nm and in particular from 10 μm to 10 nm.

The fillers according to the invention may or may not be surface-coated, in particular surface-treated with silicones, amino acids, fluoro derivatives or any other substance that promotes the dispersion and compatibility of the filler in the composition.

Mineral Fillers

For the purposes of the present invention, the terms "mineral" and "inorganic" are used interchangeably.

Among the non-pigmentary mineral fillers that may be used in the compositions according to the invention, mention may be made of talc, mica, silica, perlite, which is especially commercially available from the company World Minerals Europe under the trade name Perlite P1430, Perlite P2550 or Perlite P204, kaolin, precipitated calcium carbonate, magnesium carbonate, magnesium hydrogen carbonate, hydroxyapatite, boron nitride, hollow silica microspheres (Silica Beads® from Maprecos), and glass or ceramic microcapsules, and mixtures thereof.

According to one embodiment, the cosmetic composition according to the invention comprises at least one non-pigmentary mineral filler chosen from the group comprising kaolin, talc, silica, perlite and clay, and mixtures thereof.

Organic Fillers

Among the organic fillers that may be mentioned are polyamide powder (Orgasol® Nylon® from Atochem), poly-β-alanine powder and polyethylene powder, lauroyllysine, starch, tetrafluoroethylene polymer powders (Teflon®), hollow polymer microspheres such as those of polyvinylidene chloride/acrylonitrile, for instance Expancel® (Nobel Industrie) or of acrylic acid copolymer (such as Polytrap (Dow Corning)), acrylate copolymers, PMMA, 12-hydroxystearic acid oligomer stearate and silicone resin microbeads (for example Tospearls® from Toshiba), magnesium carbonate, magnesium hydrogen carbonate, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, and mixtures thereof.

For the purposes of the present invention, the organic fillers are different from the pigments.

They may also be particles comprising a copolymer, the said copolymer comprising trimethylol hexyl lactone. In particular, it may be a hexamethylene diisocyanate/trimethylol hexyl lactone copolymer. Such particles are especially commercially available, for example under the name Plastic Powder D-400® or Plastic Powder D-800® from the company Toshiki.

According to one embodiment, a composition of the invention may comprise at least one filler chosen from talc, silica, starch, clay, kaolin and perlite, and mixtures thereof.

One or more dispersants may be used, where appropriate, to protect the dispersed fillers or particles against aggregation or flocculation. They may be added independently of the solid fillers or particles or in the form of a colloidal dispersion of particles.

The concentration of dispersants is chosen so as to obtain satisfactory dispersion of the solid particles (without flocculation).

This dispersant may be a surfactant, an oligomer, a polymer or a mixture of several thereof, bearing one or more functionalities with strong affinity for the surface of the particles to be dispersed. In particular, poly(12-hydroxystearic acid) esters are used, such as poly(12-hydroxystearic acid) stearate with a molecular weight of about 750 g/mol, such as the product sold under the name Solsperse 21 000® by the company Avecia, esters of poly(12-hydroxystearic acid) with polyols such as glycerol or diglycerol, such as polyglyceryl-2 dipolyhydroxystearate (CTFA name) sold under the reference Dehymuls PGPH® by the company Henkel (or diglyceryl poly(12-hydroxystearate)), or alternatively poly(12-hydroxystearic acid), such as the product sold under the reference Arlacel P100 by the company Uniqema, and mixtures thereof.

As other dispersants that may be used in the composition of the invention, mention may be made of quaternary ammonium derivatives of polycondensate fatty acids, for instance Solsperse 17 000® sold by the company Avecia, and mixtures of polydimethylsiloxane/oxypropylene such as those sold by the company Dow Corning under the references DC2-5185 and DC2-5225 C.

A composition of the invention should be cosmetically and dermatologically acceptable, i.e. it should contain a non-toxic physiologically acceptable medium that can be applied to human lips. For the purposes of the invention, the term "cosmetically acceptable" refers to a composition of pleasant appearance, odour and feel.

The composition according to the invention may also contain ingredients commonly used in cosmetics, such as vitamins, thickeners, trace elements, softeners, sequestrants, fragrances, acidifying agents, basifying agents, preserving agents, sunscreens, surfactants, antioxidants, hair-loss counteractants, antidandruff agents and propellants, or mixtures thereof.

Needless to say, a person skilled in the art will take care to select this or these optional additional compounds, and/or the amount thereof, such that the advantageous properties of the corresponding composition according to the invention are not, or are not substantially, adversely impaired by the envisaged addition.

According to another aspect, the invention also relates to a cosmetic assembly comprising:

i) a container delimiting at least one compartment, the said container being closed by a closing member; and ii) a composition placed inside the said compartment, the composition being in accordance with the invention.

The container may be in any adequate form. It may especially be in the form of a bottle, a tube, a jar, a case, a box, a sachet or a carton.

The closing member may be in the form of a removable stopper, a lid, a cap, a tear-off strip or a capsule, especially of the type comprising a body attached to the container and a cover cap articulated on the body. It may also be in the form of a member for selectively closing the container, especially a pump, a valve or a flap valve.

The container may be combined with an applicator, especially in the form of a brush comprising an arrangement of bristles maintained by a twisted wire. Such a twisted brush is described especially in U.S. Pat. No. 4,887,622. It may also be in the form of a comb comprising a plurality of application members, obtained especially by moulding. Such combs are described, for example, in patent FR 2 796 529. The applicator may be in the form of a fine brush, as described, for example, in patent FR 2 722 380. The applicator may be in the form of a block of foam or of elastomer, a felt or a spatula. The applicator may be free (tuft or sponge) or securely fastened to a rod borne by the closing member, as described, for example, in U.S. Pat. No. 5,492,426. The applicator may be securely fastened to the container, as described, for example, in patent FR 2 761 959.

The product may be contained directly in the container, or indirectly. By way of example, the product may be arranged on an impregnated support, especially in the form of a wipe or a pad, and arranged (individually or in plurality) in a box or in a sachet. Such a support incorporating the product is described, for example, in patent application WO 01/03538.

The closing member may be coupled to the container by screwing. Alternatively, the coupling between the closing member and the container is done other than by screwing, especially via a bayonet mechanism, by click-fastening, gripping, welding, bonding or by magnetic attraction. The term "click-fastening" in particular means any system involving the crossing of a bead or cord of material by elastic deformation of a portion, especially of the closing member, followed by return to the elastically unconstrained position of the said portion after the crossing of the bead or cord.

The container may be at least partially made of thermoplastic material. Examples of thermoplastic materials that may be mentioned include polypropylene or polyethylene.

Alternatively, the container is made of non-thermoplastic material, especially glass or metal (or alloy).

The container may have rigid walls or deformable walls, especially in the form of a tube or a tubular bottle.

The container may comprise means for distributing or facilitating the distribution of the composition. By way of example, the container may have deformable walls so as to allow the composition to exit in response to a positive pressure inside the container, this positive pressure being caused by elastic (or non-elastic) squeezing of the walls of the container. Alternatively, especially when the product is in the form of a stick, the product may be driven out by a piston mechanism. Still in the case of a stick, especially of makeup product (lipstick, foundation, etc.), the container may comprise a mechanism, especially a rack mechanism, a threaded-rod mechanism or a helical groove mechanism, and may be capable of moving a stick in the direction of the said aperture. Such a mechanism is described, for example, in patent FR 2 806 273 or in patent FR 2 775 566. Such a mechanism for a liquid product is described in patent FR 2 727 609.

The container may be formed from a carton with a base delimiting at least one housing containing the composition, and a lid, especially articulated on the base, and capable of at least partially covering the said base. Such a carton is described, for example, in patent application WO 03/018423 or in patent FR 2 791 042.

The container may be equipped with a drainer arranged in the region of the aperture of the container. Such a drainer makes it possible to wipe the applicator and possibly the rod to which it may be securely fastened. Such a drainer is described, for example, in patent FR 2 792 618.

The composition may be at atmospheric pressure inside the container (at room temperature) or pressurized, especially by means of a propellant gas (aerosol). In the latter case, the container is equipped with a valve (of the type used for aerosols).

The present invention also relates to a cosmetic product for making up and/or caring for keratin materials, comprising at least two compositions that can be applied successively to keratin materials, especially to the lips.

The present invention also relates to a process for making up the face and the body using these two compositions. They are preferably applied successively to the keratin materials: the first composition and then the second composition.

These two compositions are conventionally known as a topcoat and a basecoat.

Thus, according to this embodiment, the invention relates to a product (also known as a kit) for making up and/or caring for keratin materials, especially the lips, comprising a first composition and a second composition conditioned in separate containers, the first composition containing, in a physiologically acceptable medium:

a) a siloxane resin comprising the following units:
(i) $(R^1_3SiO_{1/2})_a$
(ii) $(R^2_2SiO_{2/2})_b$
(iii) $(R^3SiO_{3/2})_c$ and
(iv) $(SiO_{4/2})_d$ with $R^1$, $R^2$ and $R^3$ independently representing an alkyl group containing from 1 to 8 carbon atoms, an aryl group, a carbinol group or an amino group, a being between 0.05 and 0.5,
b being between 0 and 0.3,
c being greater than 0,
d being between 0.05 and 0.6,
a+b+c+d=1, on condition that more than 40 mol % of the groups $R^3$ of the siloxane resin are propyl groups, and b) at least one phenyl silicone oil, and the second composition, which is different from the first, comprising at least one fatty substance.

The fatty substance of the second composition is preferably chosen from waxes and non-volatile oils.

According to one preferred embodiment, the second composition comprises at least one wax and at least one non-volatile oil.

Advantageously, the wax is a sunflower wax.

Preferably, the non-volatile oil is an oil such as caprylic/capric acid triglycerides.

The presence of a second composition applied over the first composition onto the keratin materials can especially improve the gloss and/or comfort properties.

The content of all the patents or patent applications cited previously is incorporated by reference into the present patent application.

In the patent application, unless specifically mentioned otherwise, the contents are expressed on a weight basis relative to the total weight of the composition.

The invention is illustrated in greater detail by the examples described below, which are given as non-limiting illustrations. The percentages are weight percentages.

EXAMPLE 1

Preparation of the Siloxane Resins

The following resins are used:

MQ resin=an MQ resin of formula $M_{0.43}Q_{0.57}$ and of $M_n$=3230 dissolved in xylene to a proportion of 70.8% by weight of solids. The MQ resin was manufactured according to the techniques described by Daudt in patent U.S. Pat. No. 2,676,182.

T Propyl resin=a propyl silsesquioxane resin at 74.8% by weight in toluene. The propyl silsesquioxane resin was obtained by hydrolysis of propyltrichlorosilane.

Preparation of the $MQT^{Pr}$ Resins

An MQ resin, a T propyl resin, xylene and 1M KOH in water in the proportions presented in Table 1 are introduced into a 3-necked flask equipped with a stirrer, a temperature probe and Dean-Stark apparatus mounted with a condenser. Xylene is pre-introduced into the Dean-Stark apparatus so as to ensure maintenance of a level of solids of 50% in the reactor. The mixture in the reactor is refluxed (between 100 and 140° C.) for at least 3 hours. Any water formed in the reaction mixture is continuously removed and trapped in the form of an azeotrope in the Dean-Stark apparatus. After refluxing for 3 hours, the water is removed from the apparatus and heating is continued for a further 30 minutes. After cooling the mixture, an excess of acetic acid is added to neutralize the KOH in the mixture. The mixture is then filtered to remove the salts formed, by passing it through a filter under pressure. Solvent exchange is performed by heating the mixture in a rotary evaporator under vacuum. After removing the majority of the xylene, decamethylcyclopentasiloxane (or isododecane) is added while continuing to remove any residual aromatic solvent. The structures of the resulting siloxane resins are characterized by $^{29}Si$ NMR and GPC, and the results are summarized in Table 2 below.

TABLE 1

| Example # | Mass ratio of MQ/$T^{Pr}$ resins added | Weight % of MQ resin | Weight % of T propyl resin | Weight % of xylene | Weight % of 1M KOH | Weight % of acetic acid |
|---|---|---|---|---|---|---|
| 1-a | (85:15) | 59.4 | 10.5 | 29.1 | 0.9 | 0.2 |
| 1-b | (50:50) | 34.9 | 34.8 | 29.1 | 0.9 | 0.2 |
| 1-c | (30:70) | 20.9 | 48.8 | 29.2 | 0.9 | 0.2 |
| 1-d | (95:5) | 67.1 | 3.5 | 28.3 | 0.9 | 0.2 |
| 1-e | (100:0) | 69.3 | 0 | 28.8 | 0.9 | 0.2 |

TABLE 2

| Example # | Resin structure according to NMR characterization | Weight % of OH | Mn | Mw | Mw/Mn |
|---|---|---|---|---|---|
| MQ resin | $M^{0.43}Q^{0.57}$ | | 3230 | 1516 | 4.7 |
| T Propyl resin | $T^{Pr}_{1.0}$ | 7.0 | 3470 | 11400 | 3.3 |
| 1-a | $M_{0.374}Q_{0.529}{:}T^{Pr}_{0.097}$ | 1.4 | 5880 | 271000 | 46.1 |
| 1-b | $M_{0.248}Q_{0.341}{:}T^{Pr}_{0.412}$ | 2.1 | 6640 | 3860000 | 581.3 |
| 1-c | $M_{0.162}Q_{0.217}{:}T^{Pr}_{0.621}$ | 1.5 | 7600 | 25300000 | 3329 |
| 1-d | $M_{0.419}Q_{0.5485}{:}T^{Pr}_{0.03}$ | 1.5 | | | |
| 1-e | MQ | 1.7 | 5200 | 28900 | 5.6 |

EXAMPLE 2

Liquid Lipstick

The following lipstick formulation was prepared:

| Compounds | Trade name and supplier | Weight percentages % |
|---|---|---|
| MQ-T propyl resin (30/70) in isododecane, as prepared in Example 1-C above | Dow Corning | 64.7 |
| Dimethicone (and) dimethicone crosspolymer | Dow Corning 9041 Silicone Elastomer Blend from Dow Corning | 2.8 |
| Dimethicone | Dow Corning 200 Fluid 5 CST from Dow Corning | 3.5 |
| Trimethylpentaphenyl-trisiloxane | Dow Corning PH-1555 HRI Cosmetic Fluid from Dow Corning | 9.5 |
| Isododecane | Isododecane from Ineos | 8.22 |
| Red 7 | Unipure Red LC 3079 OR from LCW (Sensient) | 0.23 |
| Iron oxides | Sunpuro Black Iron Oxide C33-7001 from SUN | 0.05 |
| Mica (and) titanium dioxide (and) iron oxides | Cloisonne Sparkle Gold 222 J from Engelhard (BASF) | 1 |
| Calcium aluminium borosilicate (and) silver | Metashine ME 2040 PS from Nippon Sheet Glass | 2.5 |
| Silica dimethyl silylate | Aerosil R 972 from Evonik Degussa | 7 |
| Silica | Aerosil 200 from Evonik Degussa | 0.5 |
| | | 100 |

Procedure:

a. The fillers and pigments optionally present are ground in part of the oily phase.
b. The rest of the liposoluble ingredients are then mixed together at a temperature of about 100° C. The ground mixture is then added to the oily phase.
c. The mixture is stirred with a Rayneri blender for 45 minutes, and the siloxane resin is added at room temperature.
d. The formulation is poured into isododecane-leaktight heating bags.

The composition obtained forms a glossy, long-lasting and comfortable deposit on the lips.

EXAMPLE 3

Liquid Lipstick

The following lipstick formulation was prepared (the same preparation procedure as that described previously).
It contains, inter alia, two phenyl silicone oils.

| Compounds | Trade name and supplier | Weight percentages % |
|---|---|---|
| MQ-T propyl resin (30/70) in isododecane, as prepared in Example 1-C above | Dow Corning | 52.34 |
| Dimethicone (and) dimethicone crosspolymer | Dow Corning 9041 Silicone Elastomer Blend from Dow Corning | 1.95 |
| Dimethicone | Dow Corning 200 Fluid 5 CST from Dow Corning | 2.44 |
| Trimethylsiloxyphenyl-dimethicone | Wacker-Belsil PDM 1000 from Wacker | 20 |
| Phenyl trimethicone | Dow Corning 556 Cosmetic Grade Fluid from Wacker | 9.5 |
| Titanium dioxide | Tipaque PF-671 (Cosmetic Grade) from Ishihara Sangyo | 2.74 |
| Red 7 | Unipure Red LC 3079 OR from LCW (Sensient) | 0.54 |
| Blue 1 lake | FD&C Blue 1 AL Lake 300540 from LCW (Sensient) | 0.16 |
| Iron oxides | Sunpuro Black Iron Oxide C33-7001 from SUN | 0.25 |

-continued

| Compounds | Trade name and supplier | Weight percentages % |
|---|---|---|
| Yellow 6 lake | Suncroma FD&C YEL 6 AL LK C70-5270 from SUN | 2.58 |
| Mica (and) titanium dioxide (and) iron oxides | Cloisonne Sparkle Gold 222 J from Engelhard (BASF) | 2 |
| Silica dimethyl silylate | Aerosil R 972 from Evonik Degussa | 5 |
| Silica | Aerosil 200 from Evonik Degussa | 0.5 |
| | | 100 |

The composition obtained forms a glossy, long-lasting and comfortable deposit on the lips.

The invention claimed is:

1. A process for making up and/or caring for keratin materials, comprising: applying to the keratin materials, a composition comprising, in a physiologically acceptable medium:

a) a siloxane resin comprising the following units:
(i) $(R^1{}_3SiO_{1/2})_a$
(ii) $(R^2{}_2SiO_{2/2})_b$
(iii) $(R^3SiO_{3/2})_c$ and
(iv) $(SiO_{4/2})_d$
wherein
$R^1$, $R^2$ and $R^3$ are each independently an alkyl group containing from 1 to 8 carbon atoms, an aryl group, a carbinol group or an amino group,
a is between 0.05 and 0.5,
b is between 0 and 0.3,
c is greater than 0,
d is between 0.05 and 0.6,
a+b+c+d=1,
with the proviso that more than 40 mol % of the groups $R^3$ of the siloxane resin are propyl groups; and
b) at least one phenyl silicone oil.

2. The process for making up and/or caring for keratin materials according to claim 1, wherein the siloxane resin comprises the following units:
(i) $(R^1{}_3SiO_{1/2})_a$
(iii) $(R^3SiO_{3/2})_c$ and
(iv) $(SiO_{4/2})_d$
wherein
$R^1$ and $R^3$ each independently is an alkyl group containing from 1 to 8 carbon atoms,
a is between 0.05 and 0.5,
c is greater than zero,
d is between 0.05 and 0.6,
a+b+c+d=1,
with the proviso that more than 40 mol % of the groups $R^3$ of the siloxane resin are propyl groups.

3. The process for making up and/or caring for keratin materials according to claim 1 wherein the siloxane resin is obtained via a process comprising reacting:

A) an MQ resin comprising at least 80 mol % of units $(R^1{}_3SiO_{1/2})_a$ and $(SiO_{4/2})_d$
wherein
$R^1$ is a methyl group,
a and d are greater than zero,
a ratio a/d is between 0.5 and 1.5;
and
B) a T propyl resin comprising at least 80 mol % of units $(R^3SiO_{3/2})_c$,
wherein
$R^3$ is a propyl group,
c is greater than zero,
and a mass ratio A/B is between 95/5 and 15/85.

4. The process for making up and/or caring for keratin materials according to claim 1, wherein the phenyl silicone oil is selected from the phenyl silicones of formula (VII):

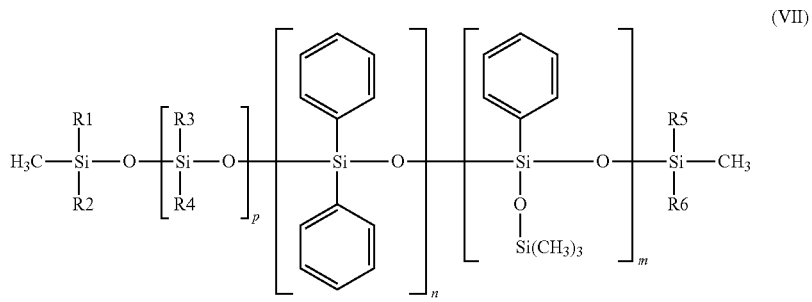

wherein
R1 to R6, independently of each other, are saturated or unsaturated, linear, cyclic or branched C1-C30 hydrocarbon-based radicals,
m, n and p are, independently of each other, integers between 0 and 100, with the proviso that n+m is between 1 and 100.

5. The process for making up and/or caring for keratin materials according to claim 1, wherein
R1 to R6, independently of each other, represent a saturated linear or branched C1-C30 and especially C1-C12 hydrocarbon-based radical
m=1 or 2 or 3, and/or n=0 and/or p=0 or 1.

6. The process for making up and/or caring for keratin materials according to claim 1, wherein the phenyl silicone oil is a phenyl trimethicone or a diphenyl dimethicone.

7. The process for making up and/or caring for keratin materials according to claim 1, wherein a content of the phenyl silicone oil is from 0.5% to 70% by weight relative to the total weight of the composition.

8. The process for making up and/or caring for keratin materials according to claim 1, wherein a total resins solids content of the siloxane resin is from 1% to 80% by weight relative to the total weight of the composition.

9. The process for making up and/or caring for keratin materials according to claim 1, wherein the composition comprises less than 3% by weight of water relative to the total weight of the composition.

10. The process for making up and/or caring for keratin materials according to claim 1, wherein the composition further comprises at least one structuring agent selected from the group consisting of thickeners, organogelling agents, waxes, pasty fatty substances and gums.

11. The process for making up and/or caring for keratin materials according to claim 1, wherein the composition further comprises at least one film-forming polymer.

12. The process for making up and/or caring for keratin materials according to claim 1, wherein the composition further comprises at least one other volatile and/or non-volatile oil, other than the phenyl silicone oil.

13. The process for making up and/or caring for keratin materials according to claim 1, wherein the composition further comprises at least one dyestuff and/or at least one filler.

14. A composition for making up and/or caring for keratin materials, comprising, in a physiologically acceptable medium:
  a) a siloxane resin comprising the following units:
  (i) $(R^1_3SiO_{1/2})_a$
  (ii) $(R^2_2SiO_{2/2})_b$
  (iii) $(R^3SiO_{3/2})_c$ and
  (iv) $(SiO_{4/2})_d$
  $R^1$, $R^2$ and $R^3$ are each independently an alkyl group containing from 1 to 8 carbon atoms, an aryl group, a carbinol group or an amino group,
  a is between 0.05 and 0.5,
  b is between 0 and 0.3,
  c is greater than 0,
  d is between 0.05 and 0.6,
  $a+b+c+d=1$,
  with the proviso that more than 40 mol % of the groups $R^3$ of the siloxane resin are propyl groups, and
  b) at least one phenyl silicone oil.

15. A product for making up and/or caring for keratin materials, comprising a first composition and a second composition conditioned in separate containers;
  wherein
    the first composition comprises, in a physiologically acceptable medium:
    a) a siloxane resin comprising the following units:
    (i) $(R^1_3SiO_{1/2})_a$
    (ii) $(R^2_2SiO_{2/2})_b$
    (iii) $(R^3SiO_{3/2})_c$ and
    (iv) $(SiO_{4/2})_d$
  wherein
    $R^1$, $R^2$ and $R^3$ are each independently an alkyl group containing from 1 to 8 carbon atoms, an aryl group, a carbinol group or an amino group,
    a is between 0.05 and 0.5,
    b is between 0 and 0.3,
    c is greater than 0,
    d is between 0.05 and 0.6,
    $a+b+c+d=1$,
    with the proviso that more than 40 mol % of the groups $R^3$ of the siloxane resin are propyl groups; and
    b) at least one phenyl silicone oil;
  and the second composition, which is different from the first, comprising at least one fatty substance.

* * * * *